United States Patent [19]

Hopfgartner et al.

[11] Patent Number: 4,652,442
[45] Date of Patent: Mar. 24, 1987

[54] PROCESS OF PRODUCING A SUSTAINED RELEASE PREPARATION CONTAINING INDOMETHACIN OR NIOMETHACIN

[75] Inventors: Johann Hopfgartner, Spittal/Drau; Wilhelm Hurka, Lieserbrücke; Otto Grablowitz, Spittal/Drau; Wolfgang Kropp, Seeboden, all of Austria

[73] Assignee: ARCANA chem. pharm. Fabrik Gesellschaft m.b.H., Spittal/Drau, Austria

[21] Appl. No.: 624,591

[22] Filed: Jun. 26, 1984

[30] Foreign Application Priority Data

Jul. 5, 1983 [AT] Austria .................................. 2467/83
May 30, 1984 [AT] Austria .................................. 1792/84

[51] Int. Cl.$^4$ .......................... A61K 9/22; A61K 9/26; A61K 9/52
[52] U.S. Cl. ....................................... 514/420; 424/19; 424/22
[58] Field of Search ...................... 424/19, 22; 514/420

[56] References Cited

U.S. PATENT DOCUMENTS 4,173,626 11/1979 Dempski et al. ...................... 424/19
4,525,345 6/1985 Dunn et al. ............................ 424/19

FOREIGN PATENT DOCUMENTS 58-170712 10/1983 Japan .

OTHER PUBLICATIONS

Lachman et al., The Theory and Practice of Industrial Pharmacy, Lea & Febiger.

*Primary Examiner*—Stanley J. Friedman
*Attorney, Agent, or Firm*—Kurt Kelman

[57] ABSTRACT

In a process of producing a sustained release preparation containing indomethacin or niomethacin, the active ingredient in the form of a powder as well as one or more food grade substances having a solubility of at least 1 gram per 10 milliliters in an aqueous liquid at any pH value from 1 to 9 and a temperature of 37° C., and one or more food grade substances having a solubility of at least 1 gram per 100 milliliters in an aqueous liquid at any pH value from 1 to 9 and a temperature of 37° C. are thoroughly mixed and the resulting mixture is mixed with a solution of one or more food grade substances which in an aqueous liquid have (a) a solubility below 1 gram per 1000 milliliters in an aqueous liquid at any pH value from 1 to 9 and a temperature of 37° C., or (b) a solubility below 1 gram per 1000 milliliters at a pH value of 1 and a temperature of 37° C.

in an organic solvent which may contain water and is adapted to form a kneadable dough with the active ingredient and components A, B and C, said mixing is continued until a kneadable dough has been formed, said dough is subjected to a pressure of at least 2 bars and is granulated by an operation which may be performed during the application of pressure, and the resulting granules are dried and are subsequently brought in a conventional form for the intake of the preparation (tablets, dragées, capsules or the like).

6 Claims, No Drawings

PROCESS OF PRODUCING A SUSTAINED RELEASE PREPARATION CONTAINING INDOMETHACIN OR NIOMETHACIN

BACKGROUND OF THE INVENTION

1. Field of the Invention

This invention relates to a process of producing a sustained release preparation containing indomethacin or niomethacin.

Indomethacin is the commercial name of 1-(4-chlorobenzoyl)-2-methyl-5-methoxy-indolyl-3-acetic acid. Niomethacin is the commercial name of 1-nicotinoyl-2-methyl-5-methoxy-indolyl-3-acetic acid.

2. Description of the Prior Art

Indomethacin and niomethacin are known as therapeutically effective substances, which are used in the control of inflammatory diseases and are contained as active ingredients in various pharmaceutic preparations. They are effective in preventing and inhibiting the formation of granulation tissue and are valuable in the treatment of arthritic, rheumatic and similar diseases which are responsive to a treatment with antiinflammatory agents.

A treatment with the conventional pharmaceutic preparations containing indomethacin or niomethacin and consisting, e.g., of tablets or capsules requires several intakes a day. Most patients requiring a treatment with antiinflammatory agents are old and often take also various other medicaments. For this reason it is desirable to reduce the number of intakes to one intake a day, if possible. On the other hand, the treatment requires a certain serum level of the active ingredient to be maintained.

Besides, the antirheumatic drugs of this kind produce secondary effects in the stomach. In the treatment with indomethacin, said secondary effects have caused up to 20% of the patients to discontinue the therapy.

SUMMARY OF THE INVENTION

The present invention proposes for the production of a sustained release preparation containing indomethacin or niomethacin a process with which the disadvantages and problems outlined hereinbefore are avoided to a very large extent.

In accordance with the invention a process of producing a sustained release composition containing indomethacin or niomethacin is characterized in that the active ingredient in the form of a powder as well as one or more food grade substances having a solubility of at least 1 gram per 10 milliliters in an aqueous liquid at any pH value from 1 to 9 and a temperature of 37° C., such as lactose, saccharose, fructose, sorbite, mannite and xylite (component A), and one or more food grade substances having a solubility of at least 1 gram per 100 milliliters in an aqueous liquid at any pH value from 1 to 9 and a temperature of 37° C., such as methylcellulose, hydroxypropylmethylcellulose, hydroxyethylcellulose, hydroxymethylcellulose, methylhydroxyethylcellulose and ethylhydroxyethylcellulose (component B) are thoroughly mixed and the resulting mixture is mixed with a solution of one or more food grade substances (component C) which in an aqueous liquid have (a) a solubility below 1 gram per 1000 milliliters in an aqueous liquid at any pH value from 1 to 9 and a temperature of 37° C., such as ethyl cellulose, Carnauba wax and the hard wax available under the name of E-Pharma from Hoechst, or (b) a solubility below 1 gram per 1000 milliliters at a pH value of 1 and a temperature of 37° C., such as cellulose acetate phthalate, cellulose phthalate, cellulose acetate succinate and carboxymethylcellulose in an organic solvent which may contain water and is adapted to form a kneadable dough with the active ingredient and components A, B and C, said mixing is continued until a kneadable dough has been formed, said dough is subjected to a pressure of at least 2 bars and is granulated by an operation which may be performed during the application of pressure, and the resulting granules are dried and are subsequently brought in a conventional form for the intake of the preparation (tablets, dragées, capsules or the like).

To ensure that a kneadable dough can be formed by mixing the active ingredient and components A and B with a solution of component C in an organic solvent, said organic solvent should be so selected that it is a solvent for the active ingredient and components B and C and said solution should be used in such a quantity that said solvent containing component C dissolved therein will partly dissolve the active ingredient and component B.

The mixing ratio of components A, B and C will determine the release rate so that any desired release rate can be selected by the selection of the weight ratio of the three components.

In the preparation containing indomethacin as an active ingredient, the mixing weight ratio should be in the range of $$C:(B+A) = 1:10 \text{ to } 1:30$$

The weight ratio of B:A may be within 2:1 and 1:2. If B:A=2:1, the release will be rather slow. If B:A=1:2, the release will be rather fast. A release over 24 hours can preferably be achieved with the following ratio:

$$C:(B+A) = 1:12 \text{ or } 1:13$$

$$B:A = 1:1 \text{ to } 1:1.2$$

The ratio of indomethacin to the total amounts of auxiliary materials may vary within wide limits. That ratio will usually be selected between 1:50 and 3:2 on a weight basis. The lower limit of that mixing ratio is suitably 1:11.5.

In preparations containing niomethacin as an active ingredient, the mixing weight ratio should be in the range of $$C:(B + A) = 1:0.5 \text{ to } 1:5, \text{ preferably } 1:0.7 \text{ to } 1:2.5$$

In this case the weight ratio of B:A may be within 2:1 and 1:2. If B:A=2:1, the release will be rather slow. If B:A=1:2, the release will be rather fast. A release over 24 hours can preferably be achieved with the following ratio:

$$C:(B+A) = 1:1.3 \text{ or } 1:1.4$$

$$B:A = 1:1 \text{ to } 1:1.2$$

The ratio of niomethacin to the total of auxiliary materials may vary within wide limits and is suitably selected between 1:50 and 4:2 on a weight basis.

Whereas U.S. Pat. No. 4,173,626 describes a preparation in which indomethacin as an active ingredient is presented in a form in which it will be slowly released, the undesired secondary effect in the stomach which has been described hereinbefore has been observed in 32% of the patients treated with the preparation disclosed in that U.S. patent.

The sustained release preparation described in that U.S. patent and the preparation obtained in accordance with the invention are based on entirely different concepts. The U.S. patent discloses two kinds of pellets. Part of the pellets are uncoated and will release indomethacin as an active ingredient as soon as the pellets have entered the stomach. The other part of the pellets have a covering, which is slowly dissolved so that the active ingredient is slowly released.

The present invention provides a therapeutically effective preparation which is intended for oral intake and contains indomethacin or niomethacin as an active ingredient, which is slowly released so that a uniform level of the active ingredient in the serum of the patient is maintained for 24 hours. Besides, secondary effects in the stomach are avoided because the preparation is so composed that it will remain substantially intact as it passes through the stomach and will not deliver a major part of the active ingredient until the preparation has entered the intestinal tract, where the active ingredient does not produce secondary effects. On the other hand, the antiinflammatory activity is preserved. The quantity of the active ingredient which is released in the stomach is so small that a certain blood level is achieved but the concentration in the stomach will not exceed a level which is critical as regards secondary effects.

The dough which has been prepared in the process in accordance with the invention may be extruded through a die or may be passed through a roll mill or through a roll mill, in which one roll has perforations through which the dough is extruded. Alternatively, the dough may be formed into a tile, to which pressure is applied in a press. It is of special significance for the process in accordance with the invention to apply pressure to the dough throughout its volume.

The starting substances used in accordance with U.S. Pat. No. 4,369,172 are the same or similar and the object stated in said U.S. patent is the same as that underlying the present invention. But the sustained release which is achieved in accordance with that U.S. patent cannot be compared to the sustained release which is achieved by the process in accordance with the invention. This is apparent from a comparison of the subsequently described Example 1 of the process according to the invention with Example 1 of said U.S. patent.

Example 1 of U.S. Pat. No. 4,369,172 with indomethacin

Artificial juice, pH value 7.2 or less
Complete decomposition after 3 hours 40 minutes.

It is apparent from these comparison experiments that the sustained release achieved in accordance with the U.S. patent is not comparable at all to the sustained release which can be achieved with the process in accordance with the invention. The preparation in accordance with the U.S. patent rather resembles a conventional, usual galenic preparation, which is decomposed somewhat more slowly.

In the U.S. patent the actual invention is seen in the use of a special grade of hydroxypropylmethylcellulose. The use of such product is not required in accordance with the invention.

The most significant difference between the process in accordance with the invention and the process known from the U.S. patent resides in that in accordance with the invention the materials to be used are worked together with an organic solvent, which optionally contains water, so that a kneadable dough is formed, and said dough is subjected to a pressure of at least 2 bars. These process steps, which are essential for the process in accordance with the invention, are not mentioned at all in the process in U.S. patent.

DESCRIPTION OF THE PREFERRED EMBODIMENTS

The invention will now be explained more in detail in the following examples.

EXAMPLE 1

75 grams indomethacin, 75 grams hydroxypropylmethylcellulose (component B) and 87.5 grams lactose (component A) are mixed for one hour in a screw mixer. A solution of 12.5 grams ethylcellulose (component C) in 180 grams ethanol of 96% concentration is separately prepared. Successive portions of said solution are added in a screw mixer to the indomethacin-containing mixture until a kneadable dough has been obtained. The dough is processed in an extruder under a pressure of about 2 bars to form rod-shaped granules 1 mm in diameter. The granules are air-dried on trays and are subsequently crushed. The fraction between 0.8 and 1.25 mm is separated by sieving and is filled into hard gelatin capsules.

Each capsule contains 75 mg of the active ingredient.
In this example
the ratio C:(B+A) is 1:13 and
the ratio B:A is 1:1.17.

The release rate of the resulting granules has been determined:

| After | Total release |
| --- | --- |
| 1 hour | 5% |
| 2 hours | 9% |
| 4 hours | 32% |
| 6 hours | 46% |
| 8 hours | 54% |
| 12 hours | 65% |
| 24 hours | 80% |

Determination of the release rate:
This is effected in accordance with the dissolution model specified in USP XX (rotating basket method, USP XX, page 959).

1. Preparation of the receiving fluids:
   (a) Artificial gastric juice, pH 1.2 (see USP XX, page 1.105, but without an addition of pepsin.
   (b) Artificial intestinal juices, pH values 5.5 and 6.8. 3.48 grams potassium dihydrogenphosphate are dissolved in water in a graduated flask having a capacity of 100 ml. 25 ml of the resulting homogeneous solution are transferred into a beaker and mixed with 190 ml 0.2N sodium hydroxide solution and diluted with about 700 ml water. The resulting liquor is homogenized and adjusted with the aid of a pH meter to the desired pH value by an addition of 1N hydrochloric acid. The resulting mixture is entirely transferred to a graduated flask having a capacity of 1000 ml and water is added to fill the flask to the mark. The adjusted pH value of the solution must not be changed.

2. Determination Procedure

The total release is determined after 1 hour, 2 hours, 4 hours, 6 hours, 8 hours, 12 hours and 24 hours.

About 250 mg of the granules are accurately weighed and placed into a rotating basket, which is rotated at 100 ($\pm 1$) revolutions per minute. The receiving fluid is used in a quantity of 900 ml and is held by thermostat control at 37° C.$\pm 1$° C.

The receiving fluids consist of artificial gastric juice, pH 1.2, in the first hour, of artificial intestinal juice, pH 5.5, in the second hour, and of artificial intestinal juice, pH 6.8, from the beginning of the 3rd hour to the end of the 24th hour.

The entire receiving fluid is renewed after each of the intervals after which the release is determined (after 1 hour, 2 hours, 4 hours, 6 hours, 8 hours and 12 hours).

The solution that has been used for the determination is extracted five times with 20 ml chloroform. The combined organic phases are filled up to 100.00 ml. After drying with sodium sulfate, the sample solution is spectroscopically measured in quartz cells at about 320 nm against chloroform as a standard.

The change of the release rates with a change of the composition of the three components is apparent from the following Example 2.

EXAMPLE 2

Example 2 is performed like Example 1, but the following composition is used:
75 grams indomethacin, 6.25 grams ethylcellulose (component C), 75 grams hydroxypropylmethylcellulose (component B), 87.5 grams lactose (component A), 120 grams ethanol.

The following release rates were obtained:
After 1 hour: 90%
After 2 hours: 100%
The ratio of C:(B+A)=1:27
The ratio of B:A=1:1.2

EXAMPLE 3

This is carried out like Example 1 but the granules are formed in that the dough is extruded under a pressure of about 11 bars through the perforations of a perforated roll in a roll mill.

EXAMPLE 4

This is carried out like Example 1 but the dough in the form of a tile is compacted in a press under a pressure of about 8 bars. The compacted material is granulated in a granulator.

EXAMPLE 5

40 grams indomethacin, 95 grams methylcellulose (component B) and 90 grams crystalline saccharose (component A) are mixed for one hour in a screw mixer. A solution of 25 grams cellulose acetate phthalate (component C) in 250 grams isopropanol is separately prepared. Successive portions of said solution are added in a screw mixer to the indomethacin-containing mixture until a kneadable dough has been obtained. The dough is processed in an extruder under a pressure of about 3 bars to form rod-shaped granules 1 mm in diameter. The granules are air-dried on trays and are subsequently crushed. The fraction between 0.1 and 1.25 mm is separated by sieving. The dust fraction and the excessively large granules are removed. The granules are filled into hard gelatin capsules.

Each capsule contains 40 mg of the active ingredient. This composition exhibits a slow release.
The ratio C:(B+A)=1:7.4
The ratio B:A=1.06:1

EXAMPLE 6

20 grams indomethacin, 109 grams hydroxyethylcellulose (component B) and 109 grams sorbite (component A) are mixed for one hour in a screw mixer. A solution of 12 grams cellulose acetate succinate (component C) in 200 grams of a mixture of ethanol of 96% concentration and acetone (weight ratio 2:1) is separately prepared. Successive portions of said solution are added in a screw mixer to the indomethacin-containing mixture until a kneadable dough has been obtained. The dough is processed in an extruder under a pressure of about 2 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 20 mg of the active ingredient.
This composition has a medium release time of 6 to 8 hours.
The ratio C:(B+A)=1:18
The ratio B:A=1:1

EXAMPLE 7

100 grams indomethacin, 61 grams hydroxyethylmethylcellulose (component B) and 82 grams fructose (component A) are mixed for one hour in a screw mixer. A solution of 6.8 grams carboxymethylcellulose (component C) in 180 grams of an isopropanol-acetone mixture (weight ratio 2:1) is separately prepared. Successive portions of said solution are added in a screw mixer to the indomethacin-containing mixture until a kneadable dough has been obtained. The dough is processed in an extruder under a pressure of about 3 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 100 mg of the active ingredient.
This composition results in a fast release within four hours.
The ratio C:(B+A)=1:21
The ratio B:A=1:1.33

EXAMPLE 8

150 grams indomethacin, 47 grams hydroxypropylmethylcellulose (component B) and 47 grams mannite (component A) are mixed for one hour in a screw mixer. A solution of 6.25 grams cellulose acetate succinate (component C) in a mixture of 180 grams ethanol of 96% concentration and methyl ethyl ketone (weight ratio 5:1) is separately prepared. Successive portions of said solution are added in a screw mixer to the indomethacin-containing mixture until a kneadable dough has been obtained. The dough is processed in an extruder under a pressure of about 2 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 150 grams of the active ingredient.

This composition has a medium release time of 8 to 12 hours.

The ratio of C:(B+A)=1:15
The ratio of B:A=1:1

EXAMPLE 9

75 grams indomethacin, 70 grams methylcellulose (component B) and 96.25 grams lactose (component A) are mixed for one hour in a screw mixer. A solution of 8.75 grams ethyl cellulose (component C) in 180 grams of ethanol of 96% concentration, which had been denatured with methyl ethyl ketone is separately prepared. Successive portions of said solution are added in a screw mixer to the indomethacin-containing mixture until a kneadable dough has been obtained. The dough is processed in an extruder under a pressure of about 2 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 75 grams of the active ingredient.

This composition exhibits a fast release of the active ingredient within 4 to 6 hours.

The ratio C:(B+A)=1:19
The ratio B:A=1:1.38

EXAMPLE 10

75 grams niomethacin, 50 grams hydroxypropylmethylcellulose (component B) and 50 grams lactose (component A) are mixed for one hour in a screw mixer. A solution of 75 grams ethyl cellulose (component C) in 225 grams ethanol of 96% concentration is separately prepared. Successive portions of said solution are added in a screw mixer to the niomethacin-containing mixture until a kneadable dough has been obtained. The dough is processed in an extruder under a pressure of about 3 bars to form rod-shaped granules 1 mm in diameter. The granules are air-dried on trays and are subsequently crushed. The fraction between 0.8 and 1.25 mm is separated by sieving and is filled into hard gelatin capsules.

Each capsule contains 75 mg of the active ingredient.
In this Example
the ratio C:(B+A) is 1:1.34 and
the ratio B:A is 1:1

For the resulting granules and for tablets prepared from the granules, the following release rates were determined:

| After | Total release |
| --- | --- |
| Granules | |
| 1 hour | 8.2% |
| 2 hours | 12.5% |
| 4 hours | 55.3% |
| 6 hours | 70.3% |
| 8 hours | 80.8% |
| 12 hours | 90.4% |
| 24 hours | 100% |
| Tablets | |

| After | Total release |
| --- | --- |
| 1 hour | 1.6% |
| 2 hours | 2.8% |
| 4 hours | 18.3% |
| 6 hours | 28.0% |
| 8 hours | 38.5% |
| 12 hours | 54.7% |
| 24 hours | 100.0% |

The determination of the release rate, the preparation of the receiving fluids and the determination procedure were carried out as in Example 1.

The change of the release rates with a change of the composition of the three components is apparent from the following Example 11.

EXAMPLE 11

75 grams niomethacin, 50 grams ethylcellulose (component C) 50 grams hydroxypropylcellulose (component B) 50 grams lactose (component A) 150 grams ethanol.

The procedure is the same as in Example 10. This composition exhibits a faster release.

The ratio of C:(B+A)=1:2
The ratio of B:A=1.1

EXAMPLE 12

The procedure is the same as in Example 10 but the dough is extruded under a pressure of about 12 bars through the perforations of a perforated roll in a roll mill to form the granules.

EXAMPLE 13

The procedure is the same as in Example 10 but the dough is compacted in a press. The compacted material is granulated by a granulator.

EXAMPLE 14

40 grams niomethacin, 60 grams methylcellulose (component B) and 50 grams crystalline saccharose (component A) are mixed for one hour in a screw mixer. A solution of 150 grams cellulose acetate phthalate (component C) in 810 grams isopropanol is separately provided. Successive portions of said solution are added in a screw mixer to the niomethacin-containing mixture until a kneadable dough has been obtained. The dough is processed in an extruder under a pressure of about 2 bars to form rod-shaped granules 1 mm in diameter. The granules are air-dried on trays and are subsequently crushed. The fraction between 0.1 and 1.25 mm is separated by sieving. The dust fraction and the excessively large granules are removed. The granules are filled into hard gelatin capsules.

Each capsule contains 40 mg of the active ingredient.
This composition exhibits a slow release.
The ratio C:(B+A)=1:0.73
The ratio B:A=1:0.83

EXAMPLE 15

20 grams niomethacin, 70 grams hydroxyethylcellulose (component B) and 62 grams sorbite (component A) are mixed for one hour in a screw mixer. A solution of 75 grams cellulose acetate succinate (component C) in 250 grams of a mixture of ethanol of 96% concentration and acetone (weight ratio 2:1) is separately prepared. Successive portions of said solution are added in a screw mixer to the niomethacin-containing mixture until a kneadable dough has been obtained. The dough is processed in an extruder under a pressure of about 3 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 20 grams of the active ingredient.

This composition has a medium release time of 6 to 8 hours.

The ratio C:(B+A)=1:1.76
The ratio B:A=1:0.89

EXAMPLE 16

100 grams niomethacin, 40 grams hydroxyethylmethylcellulose (component B) and 47 grams fructose (component A) are mixed for one hour in a screw mixer. A solution of 45 grams carboxymethylcellulose (component C) in 225 grams of a mixture of isopropanol and acetone (weight ratio 2:1) is separately prepared. Successive portions of said solution are added in a screw mixer to the niomethacin-containing mixture until a kneadable dough has been obtained. The dough is processed in an extruder under a pressure of about 3 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 100 mg of the active ingredient.

This composition exhibits a fast release within 4 hours.

The ratio C:(B+A)=1:1.93
The ratio B:A=1:1.18

EXAMPLE 17

150 grams niomethacin, 31 grams hydroxypropylmethylcellulose (component B) and 27 grams mannite (component A) are mixed for one hour in a screw mixer. A solution of 37.5 grams cellulose acetate succinate (component C) in 225 grams of a mixture of ethanol of 96% concentration and methyl ethyl ketone (weight ratio 5:1) is separately prepared. Successive portions of said solution are added in a screw mixer to the niomethacin-containing mixture until a kneadable dough has been obtained. The dough is processed in an extruder under a pressure of about 2 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 150 mg of the active ingredient.

This composition exhibits a medium release time of 8 to 12 hours.

The ratio C:(B+A)=1:2.1
The ratio B:A=1:0.87

EXAMPLE 18

75 grams niomethacin, 47 grams methyl cellulose (component B) and 55 grams lactose (component A) are mixed for one hour in a screw mixer. A solution of 52.5 grams ethyl cellulose (component C) in 225 grams ethanol of 96% concentration, which has been denatured with methyl ethyl ketone, is separately prepared. Successive portions of said solution are added in a screw mixer to the niomethacin-containing mixture until a kneadable dough has been obtained. The dough is processed in an extruder under a pressure of about 3 bars to form rod-shaped granules 1 mm in diameter. The granules are air-dried on trays and are subsequently crushed. The fraction between 0.8 and 1.25 mm is separated by sieving. The dust fraction and the excessively large granules are removed. The granules are filled into hard gelatin capsules.

Each capsule contains 75 mg of the active ingredient.

The ratio C:(B+A)=1:1.85
The ratio B:A=1:1.17

The granules made in all Examples can alternatively be compacted with tabletting aids to form tablets.

What is claimed is:

1. A process of producing a sustained release pharmaceutical formulation in granulated form that provides prolonged plasma levels of an active ingredient selected from the group consisting of indomethacin and niomethacin and is clinically effective, comprising the steps of:

initially intimately mixing said active ingredient in the form of a powder with a component A and a component B;

said component A including at least one physiologically acceptable substance having a solubility of at least one gram per 10 milliliters in water at any pH-value from 1–9 and at a temperature of 37° C., selected from the group consisting of lactose, saccharose, fructose, sorbite, mannite and xylite; and said component B including at least one physiologically acceptable substance having a solubility of at least one gram per 100 milliliters in water at any pH-value of 1 to 9 and at a temperature of 37° C., selected from the group consisting of methyl cellulose, hydroxypropylmethylcellulose, hydroxyethylcellulose, hydroxymethylcellulose, methylhydroxyethylcellulose and ethylhydroxyethylcellulose;

thereupon, in a second step, adding a component C dissolved in an organic solvent selected from the group consisting of ethanol, isopropanol, acetone and mixtures thereof, to the resulting mixture of active ingredient and components A and B in an amount such as to form a kneadable dough, said component C including at least one physiologically acceptable substance having a solubility in water (a) of below one gram per 1000 milliliters at any pH-value of 1 to 9 and at a temperature of 37° C., selected from the group consisting of ethylcellulose, carnauba wax and a blend of esters of acids of high molecular weight with alcohols of high molecular weight; or (b) of below one gram per 1000 milliliters at a pH-value of 1 and at a temperature of 37° C. selected from the group consisting of cellulose acetate, cellulose phthalate, cellulose acetate succinate and carboxymethyl cellulose; and (c) whereupon, in a third step, the kneadable dough is subjected to a pressure of at least 2 bars prior to, or during granulation.

2. The process of producing a formulation of indomethacin according to claim 1, wherein a mixing ratio of component C to the sum of components A and B is selected to be in the range of 1:10 to 1:30, the proportion of component B to that of component A being in the range of 2:1 to 1:2.

3. The process of producing a formulation of indomethacin according to claim 1, wherein a mixing ratio of component C to the sum of components A and B is selected to be within the range of 1:12 to 1:13, the proportion of component B to that of component A being in the range of 1:1 to 1:1.2.

4. The process of producing a formulation of niomethacin according to claim 1, wherein a mixing ratio of component C to the sum of components A and B is selected to be in the range of 1:0.5 to 1:5, the proportion of component B to that of component A being in the range of 2:1 to 1:2.

5. The process of producing a formulation of niomethacin according to claim 1, wherein a mixing ratio of component C to the sum of components A and B is selected to be in the range of 1:0.7 to 1:2.5.

6. The process of producing a formulation of niomethacin according to claim 1, characterized in that a mixing ratio of component C to the sum of components A and B is selected to be in the range of 1:1.3 to 1:1.4, the proportion of component B to that of component A being in the range of 1:1 to 1:1.2.

* * * * *